(12) United States Patent
Astle

(10) Patent No.: US 6,699,437 B1
(45) Date of Patent: Mar. 2, 2004

(54) BIOASSAY CASSETTE WITH MEMORY AND METHOD OF USE

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 14 days.

(21) Appl. No.: 09/649,855

(22) Filed: Aug. 29, 2000

(51) Int. Cl.$^7$ .................................................. B02L 3/00
(52) U.S. Cl. ........................ 422/102; 422/62; 422/63; 422/67; 422/99; 422/104; 436/43; 436/46; 436/55
(58) Field of Search .............................. 422/62, 63, 64, 422/65, 66, 67, 99, 102, 104; 436/43, 44, 46, 47, 48, 55

(56) References Cited

U.S. PATENT DOCUMENTS

| | | | | |
|---|---|---|---|---|
| 5,518,686 A | * | 5/1996 | Masterson et al. ............ 422/65 |
| 5,690,892 A | * | 11/1997 | Babler et al. .................. 422/63 |
| 5,756,304 A | * | 5/1998 | Jovanovich .................. 435/34 |
| 5,869,006 A | * | 2/1999 | Fanning et al. ............... 422/67 |
| 5,871,696 A | * | 2/1999 | Roberts et al. ............... 422/65 |
| 5,985,214 A | * | 11/1999 | Stylli et al. ................... 422/65 |
| 6,082,417 A | * | 7/2000 | Horn .......................... 141/130 |
| 6,086,824 A | * | 7/2000 | Fanning et al. ............... 422/65 |
| 6,096,272 A | * | 8/2000 | Clark et al. .................. 422/64 |
| 6,136,610 A | * | 10/2000 | Polito et al. ................. 435/514 |
| 6,141,602 A | * | 10/2000 | Igarashi et al. ............. 700/226 |
| 6,148,878 A | * | 11/2000 | Ganz et al. .................. 141/129 |
| 6,194,222 B1 | * | 2/2001 | Buechler et al. ............ 436/518 |

* cited by examiner

*Primary Examiner*—Jill Warden
*Assistant Examiner*—Dwayne K Handy
(74) *Attorney, Agent, or Firm*—John H. Crozier

(57) ABSTRACT

In a preferred embodiment, a microplate cassette, including: a generally hollow housing to contain therein a plurality of microplates; and a memory device associated with the cassette and adapted to be placed in operational contact with a portion of a processing device.

11 Claims, 4 Drawing Sheets

BIOASSAY CASSETTE WITH MEMORY AND METHOD OF USE

BACKGROUND OF THE INVENTION

1. Field of the Invention

The present invention relates to bioassays generally and, more particularly, to a novel bioassay cassette with memory means.

2. Background Art

One of the methods for new drug discovery in pharmaceutical research is random drug screening. Biological assays are developed to test the mode of action for therapeutic targets. Typical targets may be cardiovascular, Alzheimer's, osteoporosis, or the like. The assays are developed to determine if a potential drug candidate has an agonist (promotes) or antagonist (inhibits) effect on the target. The assay is then used to randomly screen a variety of compounds for their effect on that target.

Today large pharmaceutical firms will have compound libraries from 500,000 to 1,000,000 compounds. Even smaller biotech firms will have libraries in excess of 100,000 individual discreet compounds. High Throughput Screening (HTS) is considered to mean screening 10,000 compounds (data points) per day. Ultra High Throughput Screening (UHTS) is considered to mean screening 100,000 compounds per day. This is the current goal of many large firms.

There are a number of typical steps each compound must go through. When multiplied by 10,000 or 100,000, every day equates to considerable data handling and coordination. At the start of the chain of events, is the number of compounds required for the assays to be run today. The specific compounds are selected from storage. They are aliquoted in the desired amount for each assay. They are normally distributed in the specific microplate for that assay. It may be a 96 well plate or a 384 well plate. There are also specific types of plates, within those two plate styles. This aliquoting from the library storage plate to the assay plate is done with a pipetting instrument. That instrument must be programmed for the desired end result.

The compound plate, from the first pipetting device, was probably made at the same time similar plates were made for other assays, using the same compound library plate. These plates may require different parameters such as, a type of plate and amount of compound. The compound plates coming from this device must now be sorted and delivered to the correct assay, or to the next device.

At the specific assay, another pipetting instrument must be set up and programmed for the specific tasks at hand. From this pipettor the plates may go to other devices, such as a plate washer, incubator, or one or more additional pipetting steps. Finally, the finished assay plate may go to a reader, of some type, to readout for the final results of the assay.

At the beginning of the day, all of the various steps were known. What processing program was to be used on each device was known down to the last step. Yet short of an intricate complicated software network, each instrument had to be programmed individually for the task at hand. While it is conceivable that all instruments could be networked, it is impractical because of the wide variety of devices. In addition it would require specific integration software for each location. Yet each device, with few exceptions, has an RS232 serial communication port. Today that is almost mandatory for devices in this use.

Accordingly, it is a principal object of the present invention to provide means associated with a memory that contains information defining the processing instructions for that plate.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a microplate cassette, comprising: a generally hollow housing to contain therein a plurality of microplates; and a memory device associated with said cassette and adapted to be placed in operational contact with a portion of a processing device.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which.

DETAILED DESCRIPTION OF THE PREFERRED EMBODIMENTS

Figure 1:
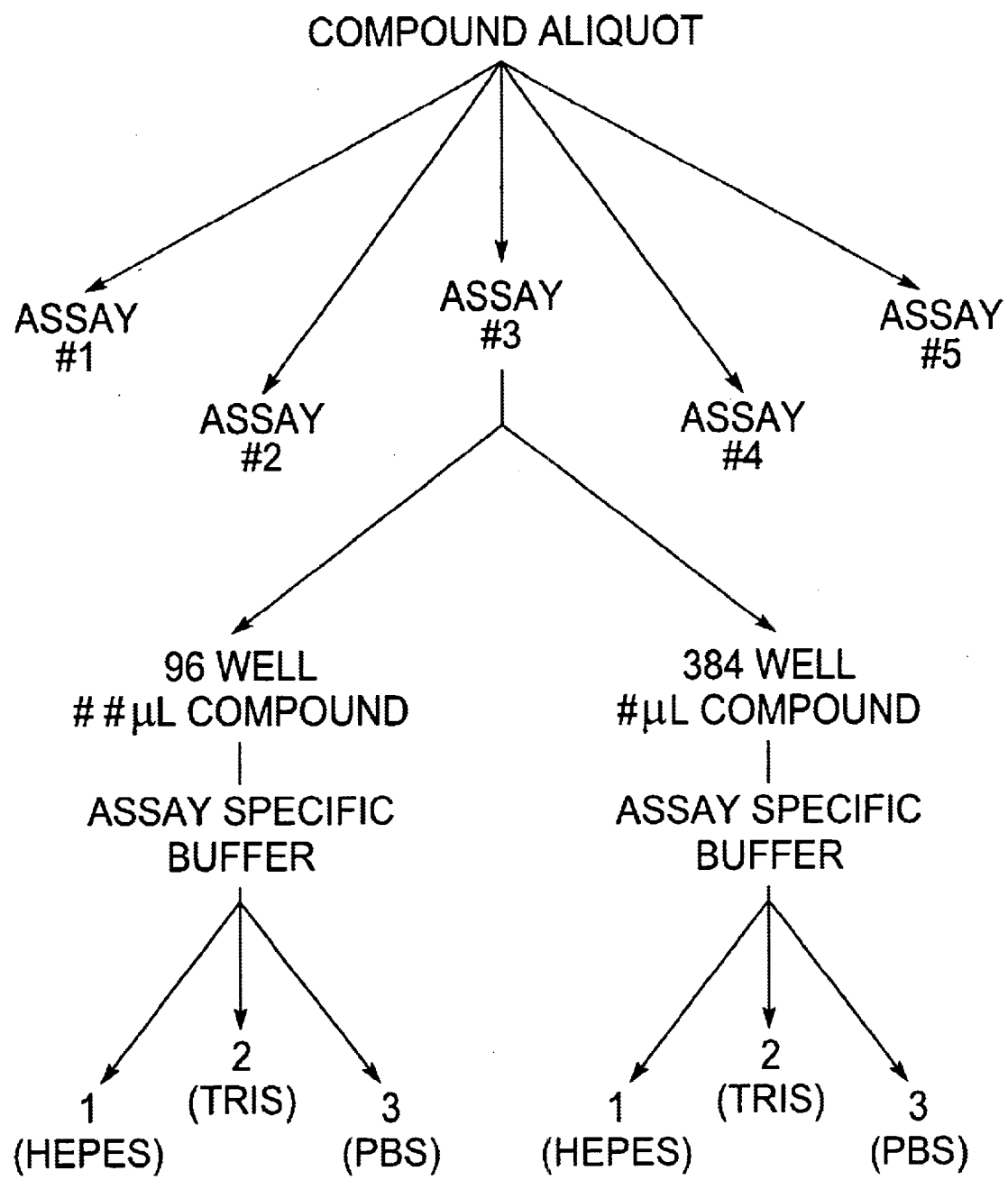
FIG. 1 is a flow diagram of the scheme of the present invention.

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

The purpose of this invention is to coordinate all of the above tasks into one simple procedure. All of the data for the processing of each plate is known somewhere at the start of the day. The objective is to consolidate that data into one file for each plate. Then have that data accompany each plate and define the processing instruction for that plate to each device. This adds considerable integrity and reliability to the entire process, particularly on high throughput operations.

This invention creates a cassette network. A simple comparison is the colloquial "sneaker network" whereby disks containing information are hand carried between computers. In this invention the transfer of data between devices is an accessible memory device carried between devices by a microplate cassette.

In the area of High Throughput Screening, and other similar cases, process work is being completed on microplates that carry the assay constituents. Each processing device completes some function on the microplate and its contents. It is then passed to the next device for the next function. To avoid handling individual microplates, they are handled as a stack of some number (typically, 25–50), in a cassette format. Embedded in the cassette is a semiconductor memory.

When the cassette is inserted into the using device, to dispense or receive microplates, electrical contact is made with the memory. The contents of the memory then may communicate with the receiving device, such as a pipetting workstation. The instructions for processing each plate are transferred to the device. Upon processing, confirmation data is passed back to the cassette memory. This maintains the audit trail and concurrently passes information onto the next processing device.

Following is an example of a typical operation. Each device to process an assay microplate would have an identifier. Within each device there are preset programs, each with its own identifier. The daily worklist defines the pathway of each plate, from device to device. Within each device it specifics the program identifier for that plate. Each plate in the system is bar coded to facilitate tracking and performance.

The empty cassette is filled by the compound plate retrieval system. It picks the compound plate by its bar code as identified by the downloaded worklist from the main database. The plate retrieval system uploads this data, along with the pathway data from the database. When the cassette is inserted into the next device on the pathway, electrical contact is made automatically at insertion. The cassette memory is downloaded into the device's systems memory. When a microplate is accessed from the cassette, its bar code label is read. This initiates the processing instructions for that specific plate. At the completion of the processing of this cassette, the confirming action taken is uploaded into the cassette memory as it is passed to the next device in the processing pathway.

A typical flow diagram of the scheme of the present invention is shown on FIG. 1. The selected compound is to be aliquoted for one or more assays. The amount of compound to be aliquoted is a variable as is the type of plate and the type of assays specific buffer to be used. At this point, the cassettes will contain plates processed and stacked by compound. They are then sorted by assay and proceed to the next step. The process then proceeds for each successive step.

From one file of work that is to be accomplished, all processing devices in the pathway are controlled to their specific function. The simple expedient of a traveling memory replaces the functionality of a complex software network. Not only is software development eliminated, but the task of wiring the interconnect is also eliminated. The net result is simplicity and most important reliability in operation.

Figure 2:
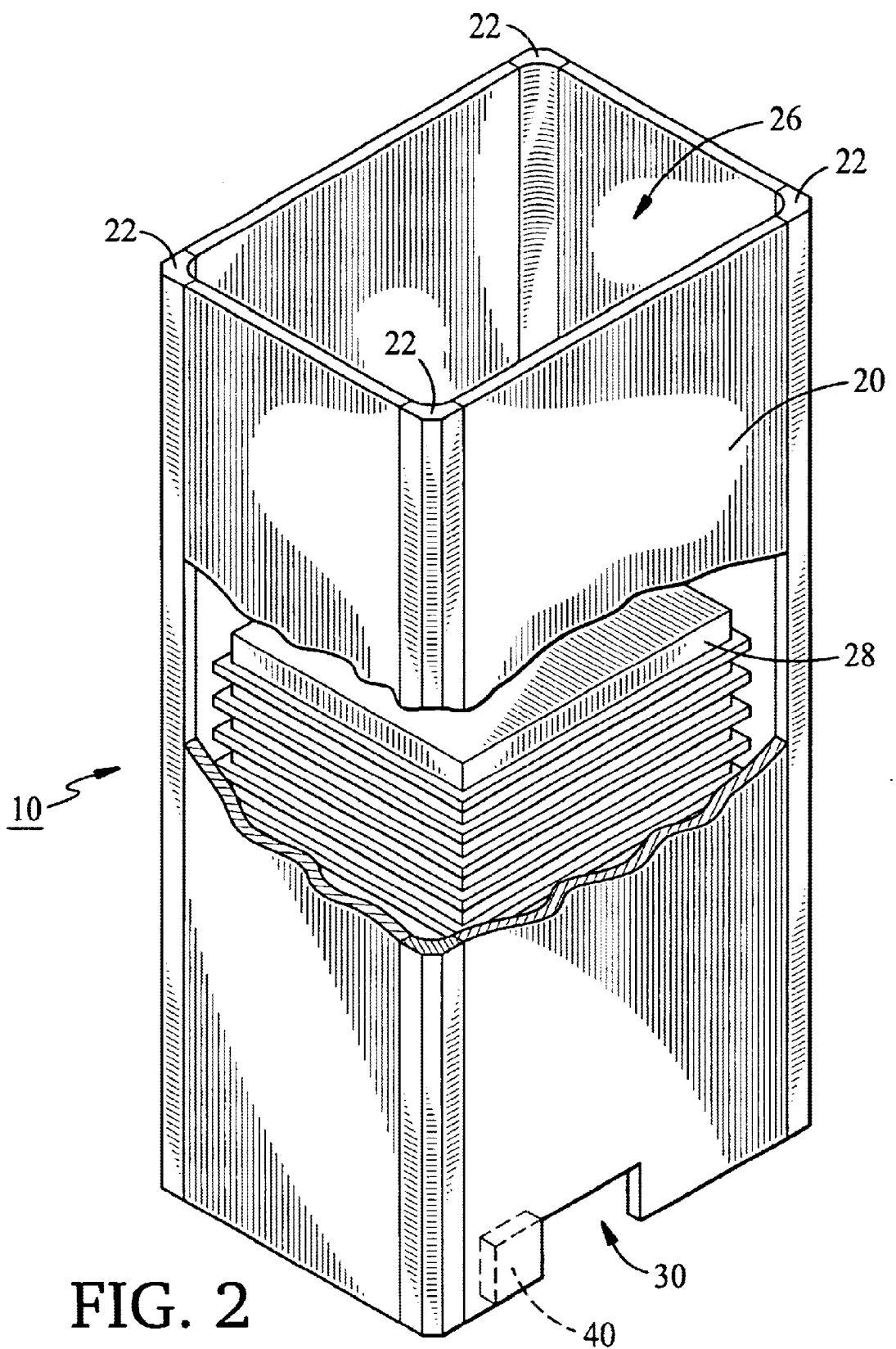
FIG. 2 is an isometric view, partially cut-away, of a microplate cassette according to the present invention.

FIG. 2 illustrates a microplate cassette, constructed according to the present invention, and generally indicated by the reference numeral 10. Cassette 10 is used to transport microplates for biological assays between processing devices and includes a housing 20 consisting of four, vertical corner posts 22 and four, vertical side walls 24 connected together to define therein an interior volume 26 in which a stack of a plurality of microplates, as at 28, is disposed. Mounted near an inner lower edge of one side wall 24, and adjacent to an opening 30 defined through the side wall, is a memory device 40 in which are programmed processing instructions for microplates 28. Memory device 40 is preferably a semiconductor read/write memory device and may be as furnished by Dallas Semiconductor of Dallas, Tex.

Figure 3:
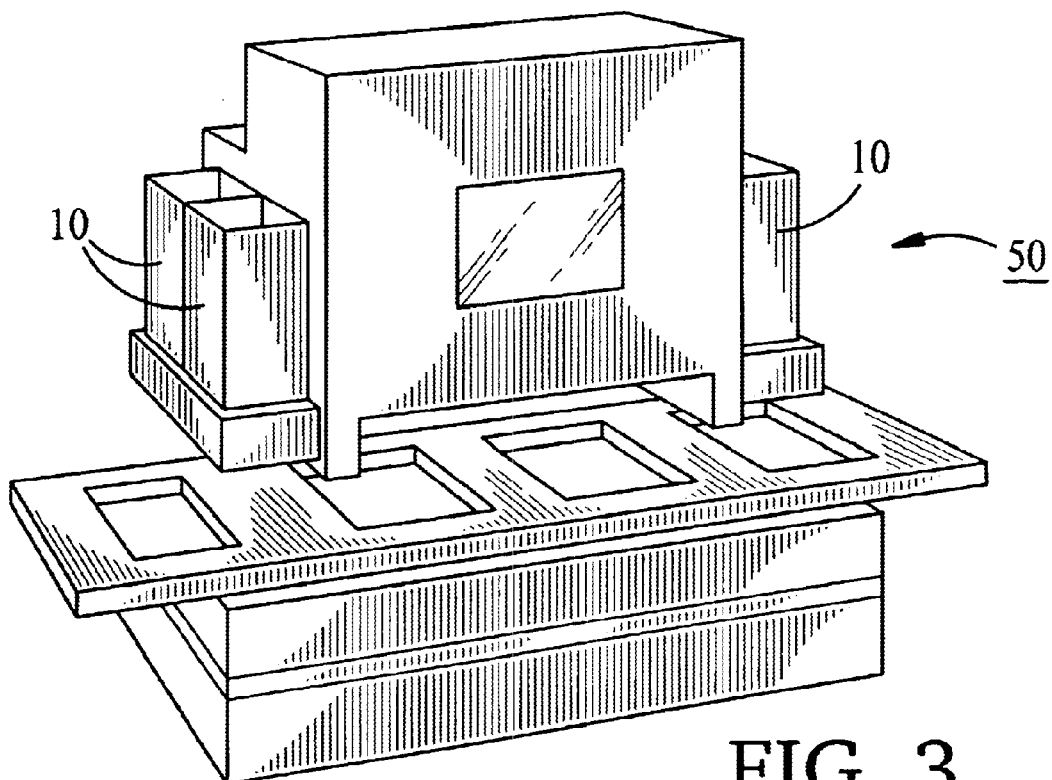
FIG. 3 is an isometric view of two cassettes positioned as infeed and outfeed devices for microplates on a processing device.

FIG. 3 illustrates a processing device generally indicated by the reference numeral 50. Processing device 50 may be a pipettor, a washer, or other type of device that performs an operation on microplates. Four cassettes 10 (FIG. 2) (only three visible on FIG. 3) serve as infeed and outfeed devices. Either the right or the left pair can serve as infeed or outfeed devices. Conventional means are employed to move microplates 28 (FIG. 2) from and to cassettes 10.

Figure 4:
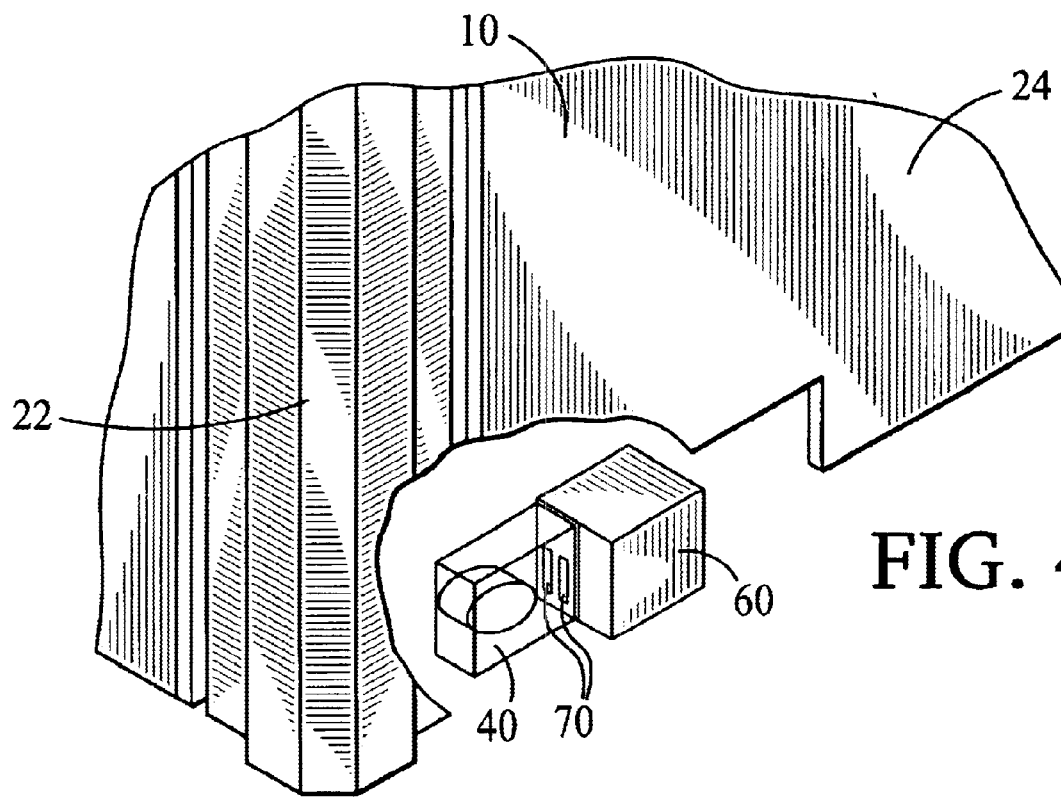
FIG. 4 is a fragmentary, isometric view, partially cut-away, of a microplate cassette, showing a memory device mounted in a cassette in contact with an orientation block in a processing device.

FIG. 4 illustrates a cassette in place on a processing device, such as processing device 50 (FIG. 3), with memory device 40 in contact with an orientation block 60 mounted on the processing device (the processing device is not otherwise shown on FIG. 4). Memory device 40 includes two contacts 70, one of which is a ground in contact with the case of the memory device and the other is connected to the face of the memory device, thereby completing the electrical interface to the memory device. When cassette 10 is mounted on a processing device, two spring loaded electrical contact fingers (not shown) wipe contacts 70 and remain in electrical contact therewith while the cassette is mounted on the processing device. This completes the electrical connection between memory device 40 and the processing device control system to download processing instructions from the memory device to the computer controlling the processing device. The microplate is then processed in accordance with the instructions obtained from memory device 40. After processing, confirmation data from the processing device is uploaded to memory device 40 over the same link. Orientation block 60 also assures that the cassette is mounted in the proper way on the processing device.

Figure 5:
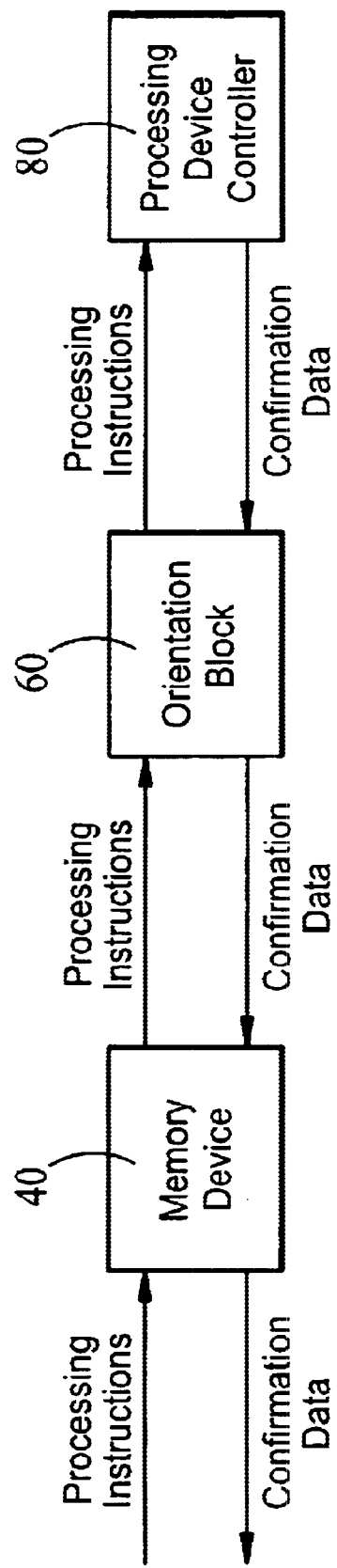
FIG. 5 is a block diagram showing the path of processing instructions and confirmation data according to the present invention.

FIG. 5 illustrates the flow of information to and from memory device 40, orientation block 60, and processing device controller 80.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction and method without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. A microplate cassette, comprising:
   (a) a generally hollow housing containing therein a plurality of microplates;
   (b) a memory device associated with said cassette and placed in operational contact with a portion of a processing device as said cassette is mounted on said processing device, said memory device transferring to said processing device processing instructions for said microplates; and
   (c) said memory device having programmed therein processing instructions for said plurality of microplates and for multiple independent processing devices.

2. A microplate cassette, as defined in claim 1, wherein: said memory device is a write/read memory device.

3. A microplate cassette, as defined in claim 1, wherein: said memory device is mounted on said housing.

4. A processing device for microplates, comprising:
   (a) at least one microplate cassette mounted on said processing device, said at least one microplate cassette containing therein a plurality of microplates for processing in said processing device;
   (b) a memory device associated with said cassette;
   (c) a portion of said processing device being in operational contact with said memory device and operatively connected to a control device in said processing device;
   (d) said memory device to transfer to said processing device processing instructions; and
   (e) said memory device having programmed therein processing instructions for said plurality of microplates and for multiple independent processing devices.

5. A microplate processing device, as defined in claim 4, wherein: said memory device is a write/read memory device.

6. A microplate processing device, as defined in claim 4, wherein: said memory device has programmed therein processing instructions for said plurality of microplates.

7. A microplate processing device, as defined in claim 4, wherein: said memory device is mounted on said housing.

8. A method of processing microplates, comprising:
   (a) providing a microplate cassette having a generally hollow housing to contain therein a plurality of said microplates and with a memory device associated with said cassette;
   (b) programming said memory device with processing instructions for said plurality of microplates for a plurality of independent processing devices;
   (c) mounting said cassette on one of said plurality of independent processing devices with said memory device in operational contact with a portion of said one of said plurality of independent processing devices;
   (d) downloading said processing instructions to a control device in said one of said independent processing devices; and
   (e) using said one of said plurality of independent processing devices to process said microplates in accordance with said processing instructions.

9. A method of processing microplates, as defined in claim 8, wherein: said memory device is a write/read memory device.

10. A method of processing microplates, as defined in claim 8, further comprising: providing confirmation data to said memory device after said one of said independent processing devices processes said microplates.

11. A method of processing microplates, as defined in claim 8, further comprising: providing said memory device mounted in said housing.

* * * * *